US011666318B2

(12) United States Patent
Otto et al.

(10) Patent No.: US 11,666,318 B2
(45) Date of Patent: Jun. 6, 2023

(54) DISTRACTION DEVICE WITH DISPOSABLE FORCE SENSOR POD

(71) Applicants: MAKO Surgical Corp., Fort Lauderdale, FL (US); OrthoSensor, Inc., Dania Beach, FL (US)

(72) Inventors: Jason Otto, Plantation, FL (US); Radu Iorgulescu, Fort Lauderdale, FL (US); Kevin Bechtold, Fort Lauderdale, FL (US); Jonathan Trousdale, Dania Beach, FL (US); Joseph Decerce, Dania Beach, FL (US)

(73) Assignees: MAKO Surgical Corp., Fort Lauderdale, FL (US); OrthoSensor, Inc., Dania Beach, FL (US)

( * ) Notice: Subject to any disclaimer, the term of this patent is extended or adjusted under 35 U.S.C. 154(b) by 309 days.

(21) Appl. No.: 17/004,773

(22) Filed: Aug. 27, 2020

(65) Prior Publication Data

US 2021/0059656 A1    Mar. 4, 2021

Related U.S. Application Data

(60) Provisional application No. 62/894,130, filed on Aug. 30, 2019.

(51) Int. Cl.
| | |
|---|---|
| *A61B 17/02* | (2006.01) |
| *A61B 34/10* | (2016.01) |
| *A61B 34/30* | (2016.01) |
| *A61B 34/20* | (2016.01) |
| *A61B 34/00* | (2016.01) |
| *G01L 1/22* | (2006.01) |

(Continued)

(52) U.S. Cl.
CPC ............ *A61B 17/025* (2013.01); *A61B 34/10* (2016.02); *A61B 34/20* (2016.02); *A61B 34/25* (2016.02); *A61B 34/30* (2016.02); *G01L 1/22* (2013.01); *A61B 34/32* (2016.02); *A61B 34/76* (2016.02); *A61B 2017/00407* (2013.01); *A61B 2017/0268* (2013.01); *A61B 2034/2055* (2016.02); *A61B 2034/2059* (2016.02); *A61B 2090/064* (2016.02); *A61B 2562/0252* (2013.01); *A61B 2562/0261* (2013.01)

(58) Field of Classification Search
CPC ..................... A61B 17/025; A61B 2017/0268
See application file for complete search history.

(56) References Cited

U.S. PATENT DOCUMENTS

| | | |
|---|---|---|
| 5,470,354 A | 11/1995 | Hershberger et al. |
| 6,859,661 B2 | 2/2005 | Tuke |

(Continued)

OTHER PUBLICATIONS

U.S. Appl. No. 62/817,355, filed Mar. 12, 2019, Mako Surgical Corp.

(Continued)

*Primary Examiner* — Nicholas W Woodall
(74) *Attorney, Agent, or Firm* — Foley & Lardner LLP

(57) ABSTRACT

A surgical system includes a disposable force sensor pod that includes a load cell and a mounting feature. The surgical system also includes a computing system configured to be placed in electronic communication with the disposable force sensor pod and receive a force measurement from the disposable force sensor pod. The disposable force sensor pod is configured to be removeably coupled to a distraction device using the mounting feature.

20 Claims, 10 Drawing Sheets

(51) Int. Cl.
    *A61B 34/32* (2016.01)
    *A61B 90/00* (2016.01)
    *A61B 17/00* (2006.01)

(56) References Cited

U.S. PATENT DOCUMENTS

| | | | |
|---|---|---|---|
| 7,412,897 B2 | 8/2008 | Crottet et al. | |
| 7,442,196 B2 | 10/2008 | Fisher et al. | |
| 7,615,055 B2 | 11/2009 | Disilvestro | |
| 7,837,691 B2 | 11/2010 | Cordes et al. | |
| 8,118,815 B2 | 2/2012 | Van Der Walt | |
| 8,162,951 B2 * | 4/2012 | Kaufman | A61F 2/4657 606/57 |
| 8,197,489 B2 | 6/2012 | Chessar et al. | |
| 8,211,041 B2 | 7/2012 | Fisher et al. | |
| 8,323,290 B2 | 12/2012 | Metzger et al. | |
| 8,337,508 B2 | 12/2012 | Lavallee et al. | |
| 8,491,589 B2 | 7/2013 | Fisher et al. | |
| 8,506,571 B2 | 8/2013 | Chana et al. | |
| 8,998,910 B2 | 4/2015 | Borja et al. | |
| 9,351,850 B2 | 5/2016 | Fischer et al. | |
| 9,439,656 B2 | 9/2016 | Chana et al. | |
| 9,538,953 B2 | 1/2017 | Sherman et al. | |
| 9,539,116 B2 | 1/2017 | Claypool et al. | |
| 9,554,745 B2 | 1/2017 | Orthosoft | |
| 9,572,588 B2 | 2/2017 | Fisher et al. | |
| 9,642,571 B2 | 5/2017 | McIntosh et al. | |
| 10,398,477 B2 * | 9/2019 | Ibrahim | A61B 17/7059 |
| 2005/0038442 A1 | 2/2005 | Freeman | |
| 2007/0066917 A1 | 3/2007 | Hodorek et al. | |
| 2007/0219561 A1 * | 9/2007 | Lavallee | A61B 90/36 606/90 |
| 2007/0244488 A1 * | 10/2007 | Metzger | A61B 17/025 606/90 |
| 2009/0018544 A1 | 1/2009 | Heavener | |
| 2012/0017276 A1 | 1/2012 | Baskar | |
| 2014/0031828 A1 * | 1/2014 | Patel | A61B 17/7077 606/90 |
| 2015/0342588 A1 | 12/2015 | Bechtold et al. | |
| 2016/0278754 A1 | 9/2016 | Todorov et al. | |
| 2016/0346044 A1 | 12/2016 | Brown et al. | |
| 2017/0156736 A1 | 6/2017 | Claypool et al. | |
| 2017/0245872 A1 | 8/2017 | Rock et al. | |
| 2017/0360512 A1 | 12/2017 | Couture et al. | |
| 2018/0049895 A1 | 2/2018 | Haight et al. | |
| 2018/0085134 A1 | 3/2018 | Uthgenannt | |
| 2018/0098774 A1 | 4/2018 | Bonutti | |
| 2019/0388078 A1 | 12/2019 | Otto et al. | |
| 2020/0352555 A1 * | 11/2020 | Ebbitt | A61B 34/10 |

OTHER PUBLICATIONS

U.S. Appl. No. 62/905,037, filed Sep. 24, 2019, Mako Surgical Corp.

* cited by examiner

US 11,666,318 B2

DISTRACTION DEVICE WITH DISPOSABLE FORCE SENSOR POD

CROSS-REFERENCE TO RELATED APPLICATIONS

This application claims the benefit of and priority to U.S. Provisional Patent Application No. 62/894,130, filed 30 Aug. 2019, the entire disclosure of which is incorporated by reference herein.

BACKGROUND

The present disclosure relates generally to surgical systems for orthopedic surgeries, and more particularly to surgical systems for total and partial knee arthroplasty procedures. Knee arthroplasty, colloquially referred to as knee replacement, is widely used to treat knee osteoarthritis and other damage to a patient's knee joint by replacing portions of the knee anatomy with prosthetic components. In a total knee arthroplasty procedure, for example, a patient's femur and tibia are typically modified to be joined to a prosthetic device using a series of cuts to prepare the surface of the bones. The prosthetic device is then coupled to the bones (e.g., a tibial component is coupled to the patient's tibia and a femoral component is coupled to the patient's femur).

One possible tool for use in total knee arthroplasty procedure is a robotically-assisted surgical system. A robotically-assisted surgical system typically includes a robotic device that is used to prepare a patient's anatomy, such as by making bone cuts, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. The surgical plan may be patient-specific. Based on the surgical plan, the surgical system guides, controls, or limits movements of the surgical tool during portions of the surgical procedure. Guidance and/or control of the surgical tool serves to protect the patient and to assist the surgeon during implementation of the surgical plan. In a knee arthroplasty operation, a robotically-assisted surgical system can be used to help carry out a surgical plan that includes making the necessary planar cuts mentioned above, for example by providing force feedback to guide a cutting tool to make the pre-planned planar cuts under surgeon control.

SUMMARY

One implementation of the present disclosure is a joint distraction device. The joint distraction devices includes a first member, a hinge coupled to the first member, and a second member comprising a distal portion and a proximal portion. The second member is coupled to the hinge at a position between the distal portion and the proximal portion. The joint distraction device includes a third member coupled to the hinge and manipulable to exert a force on the proximal portion of the second member that causes the distal portion to rotate away from the first member. The joint distraction device also includes a disposable force sensor pod configured to be removeably coupled to at least one of the second member or the third member.

Another implementation of the present disclosure is a surgical system. The surgical system includes a disposable force sensor pod that includes a mounting feature and at least one of a load cell or a strain gauge. The surgical system also includes a computing system configured to be placed in electronic communication with the disposable force sensor pod and receive a force measurement from the disposable force sensor pod. The disposable force sensor pod is configured to be removeably coupled to a distraction device by the mounting feature.

Another implementation of the present disclosure is a method. The method includes sterilizing a distraction device, obtaining a sterile package containing a disposable force sensor pod, removing the disposable force sensor pod from the sterile package, coupling the disposable force sensor pod to the distraction device, and establishing electronic communication between the disposable force sensor pod and a computing system.

DETAILED DESCRIPTION

Figure 1:
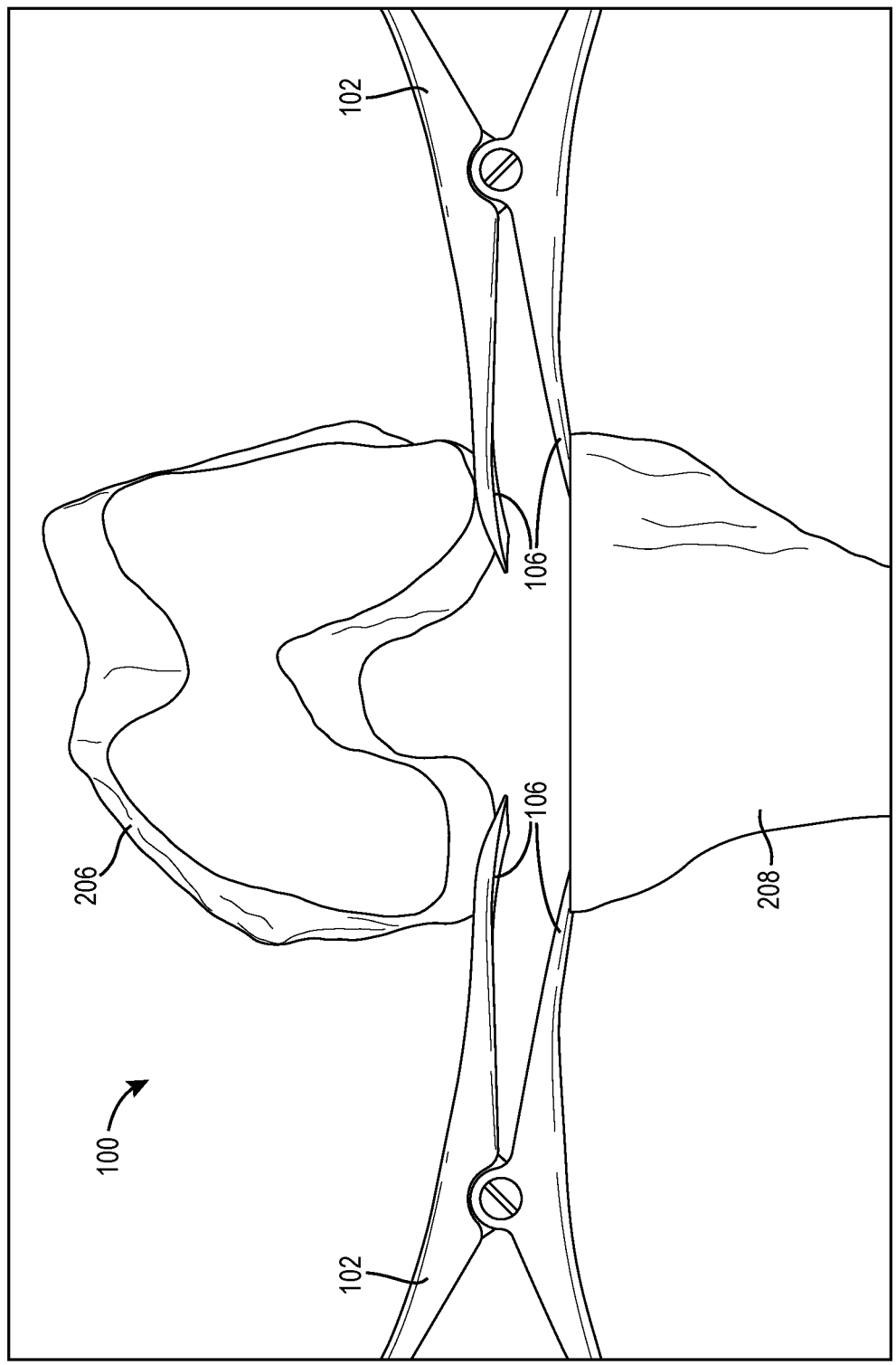
FIG. 1 is an illustration of a knee joint distracted by a pair of distraction devices, according to an exemplary embodiment.

Referring to FIG. 1, an illustration of a knee joint 100 distracted by a pair of distraction devices 102 is shown, according to an exemplary embodiment. The knee joint 100 shown in FIG. 1 is shown during an in-progress total knee arthroplasty (TKA) procedure. It should be understood that that disclosure herein may also be applicable to partial knee arthroplasty (PKA) procedures. In a TKA procedure, surfaces of a patient's tibia 208 and femur 206 are modified to facilitate coupling of the tibia 209 and the femur 206 to an artificial knee implant. The tibia 208 is prepared for coupling to a tibial component of an implant and the femur 206 is prepared for coupling to a femoral component of the implant. Bone is removed from the tibia 208 and the femur

206 to provide planar (or otherwise contoured) surfaces configured to mate with the implant components.

One goal for a TKA procedure is for the procedure to result in a proper amount of tension in the ligaments connecting the tibia and the femur to facilitate comfortable, natural movement of the knee for the patient following the procedure. Because the implant will be positioned between the tibia and the femur, various aspects of the surgical plan and the implant can affect a distance spanned by the ligaments and therefore the amount of tension in the ligaments after an operation. The size of the implant or a spacer for use with implant can be selected to tune the tension as needed. Modifications to the bone (e.g., the depth of a cut into a bone) can be tailored to achieve proper ligament tensioning. Additionally, soft tissue may be altered to release tension in ligaments to facilitate soft tissue balancing during a TKA or PKA procedure.

As shown in FIG. 1, distraction devices 102 can be used to distract (separate, force apart, etc.) the tibia 208 and the femur 206 to test ligament tension at various distraction distances (i.e., when the femur 206 and the tibia 208 are separated by various distances). In some cases, distraction devices 102 are configured for manual sensing of ligament tension, such that a surgeon can feel the tension (i.e., the force exerted by the distraction device(s) 102) and make a surgical planning decisions based on manual feel and personal experience. In some embodiments, for example as shown in FIG. 3 and described in detail with reference thereto, a distraction device 102 can include a force sensor configured to measure a distraction force provided by a distraction device 102 to the femur 206 and tibia 208. In such embodiments, the force sensor may be configured to provide force measurements to a surgical system (e.g., a robotically-assisted surgical system) for use in computer-assisted surgical planning and/or control of a robotic device as described below.

In some embodiments, the distraction device 102 is configured to provide an indication of a distance of separation as distracted by the distraction device 102 (i.e., a distance between distal ends of the working portions 106 of a distraction device 102). For example, a handle portion of a distraction device 102 may include a distance scale providing information indicative of the distance of separation as distracted by the distraction device 102. In other embodiments, a tracking system (for example as described below with reference to FIG. 2) is configured to track the relative positions of the femur 206 and the tibia 208.

One or more distraction devices 102 may be used to facilitate planning and execution of a knee arthroplasty procedure. One or more distraction devices 102 may be used individually or in combination (e.g., simultaneously) during various stages of a surgical procedure. For example, for a TKA procedure, one or more distraction devices 102 may be utilized before any bone modifications are made, after a tibial cut is made and before a femoral cut is made (or vice versa), after a tibial cut is made and between femoral cuts, and/or after the planned tibial cut and femoral cuts are made. Additionally, one or more distraction devices 102 may be used to distract the knee joint when the knee is in extension (i.e., the leg is "straight" with the tibia and the femur substantially aligned), in flexion (i.e., when the leg is "bent", for example with the tibia and the femur at an approximately right angle as shown in FIG. 1), and throughout a range of motion of the knee joint. Although the examples herein refer to TKA procedures, it should be understood that the distraction device 102 and various systems and methods described herein may be suitable and/or adaptable for use in partial knee arthroplasty procedures, total or partial hip arthroplasty procedures, other hip- or knee-related procedures, shoulder surgeries, jaw surgeries, other joint-related procedures, etc.

Figure 2:
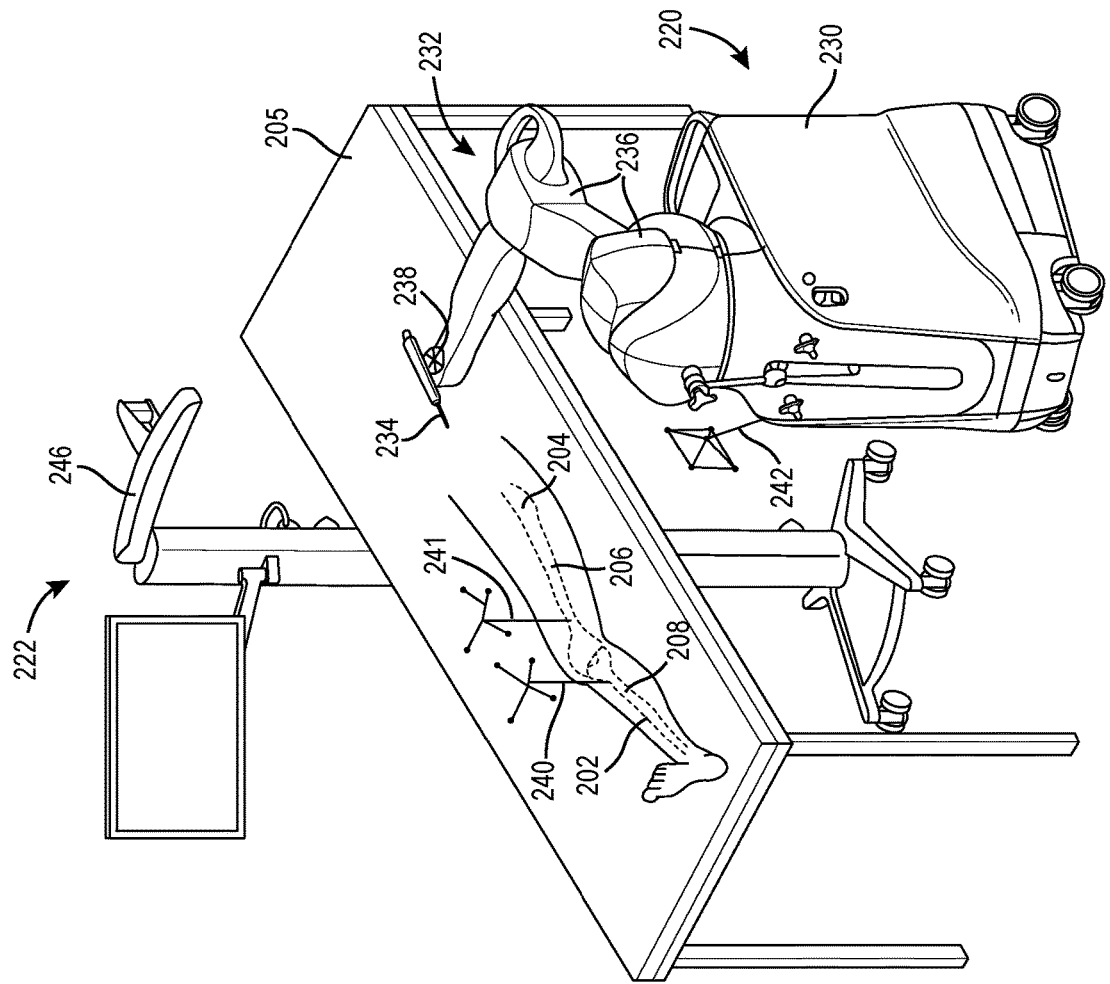
FIG. 2 is an illustration of a surgical system, according to an exemplary embodiment.
Figure 2:
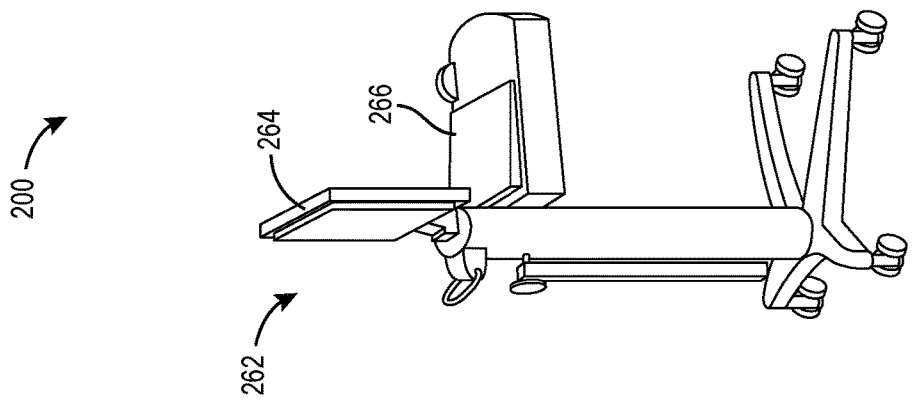

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. Leg 202 includes femur 206 and tibia 208, between which a prosthetic knee implant is to be implanted in a total knee arthroscopy procedure. To facilitate the procedure, surgical system 200 includes robotic device 220, tracking system 222, and computing system 224.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, grind, drill, partially resect, reshape, and/or otherwise modify a bone. The surgical tool 234 may be any suitable tool, and may be one of multiple tools interchangeably connectable to robotic device 220. For example, as shown in FIG. 2 the surgical tool 234 is a spherical burr. The surgical tool may also be a sagittal saw, for example with a blade aligned parallel with a tool axis or perpendicular to the tool axis.

Tracking system 222 is configured track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of cuts made by the surgical tool 234, and allow a user to visualize the femur 206, the tibia 208, the surgical tool 234, and/or the robotic arm 232 on a display of the computing system 224. More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials coupled to surgical tool 234, and a detection device 246 configured to detect the three-dimensional position of fiducials (i.e., markers on fiducial trees 240-242). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). A stereoscopic arrangement of cameras on detection device 246 allows the position of each fiducial to be determined in 3D-space through a triangulation approach. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to make a cut in or otherwise modify the anatomical feature. Additionally, using the tracking system 222 of FIG. 2 or some other approach to surgical navigation and tracking, the surgical system 200 can determine the relative positions of the femur 206 and the tibia 208 (e.g., a distance therebetween), including when a distraction device 102 is operated to distract the knee (i.e., to affect the distance between the femur 206 and the tibia 208).

The computing system 224 is configured to create a surgical plan, control the robotic device 220 in accordance with the surgical plan to make one or more surgical cuts, receive data relating to the location of the surgical tool 234, determine the location and orientation of cuts made by the surgical tool 234, alter the surgical plan based on the determinations to minimize the relative error between cuts, and control the robotic device in accordance with the updated surgical plan. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed (e.g., femur 206). The imaging data may be created using any suitable medical imaging technique to image the relevant anatomical feature, including computed tomography (CT), magnetic resonance imaging (MRI), and/or ultrasound. The imaging data is then segmented (i.e., the regions in the imaging corresponding to different anatomical features are distinguished) to obtain the virtual bone model. For example, MRI-based scan data of a knee is segmented to distinguish the femur from surrounding ligaments, cartilage, and other tissue to obtain a three-dimensional model of the imaged femur.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, as described in detail below, the surgical plan may be generated and/or modified based on distraction force measurements collected intraoperatively.

The preoperative surgical plan includes the desired cuts, holes, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. Accordingly, the processing circuit 260 may receive, access, and/or store a model of the prosthetic to facilitate the generation of surgical plans.

The processing circuit 260 is further configured to generate a control object for the robotic device 220 in accordance with the surgical plan. The control object may take various forms according to the various types of possible robotic devices (e.g., haptic, autonomous, etc). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to a "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010, 180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 and/or tibia 208 and/or support weight of the femur 206 and/or tibia 208, for example to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

The processing circuit 260 is also configured to receive distraction force measurements from a disposable force sensor pod removeably coupled to a distraction device, which may be configured as shown in FIG. 3 and described in detail below. Various functionality of the processing circuit 260 relating to distraction measurements are described in detail below with reference to FIG. 8.

Figure 3A:
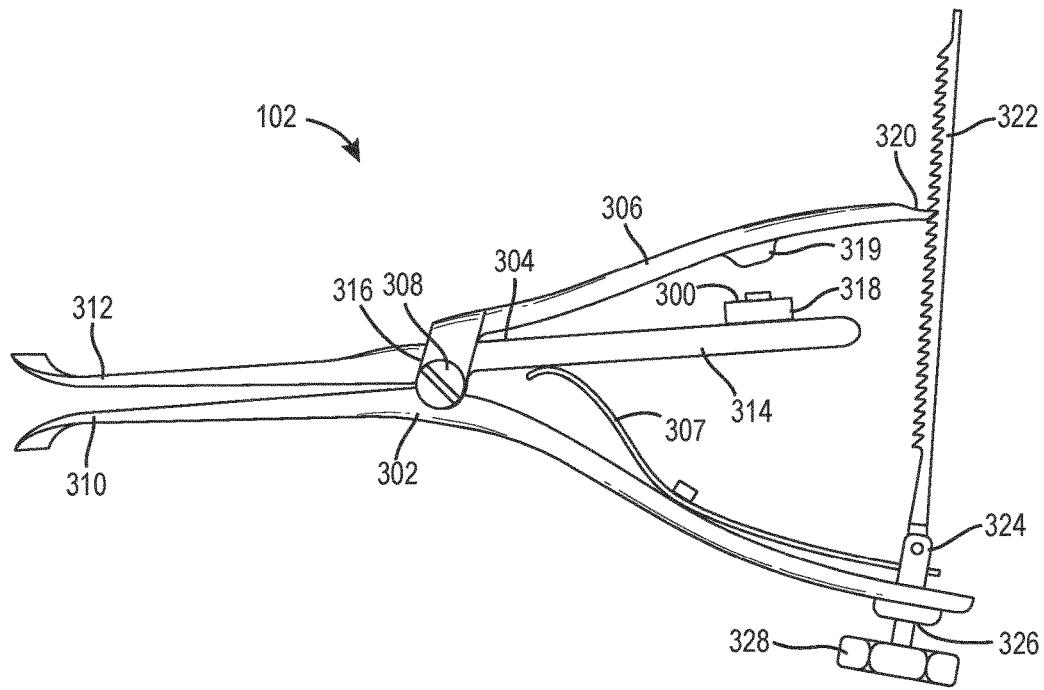
FIG. 3A is a side view of a joint distraction device with a disposable force sensor pod removeably coupled thereto, according to an exemplary embodiment.
Figure 3B:
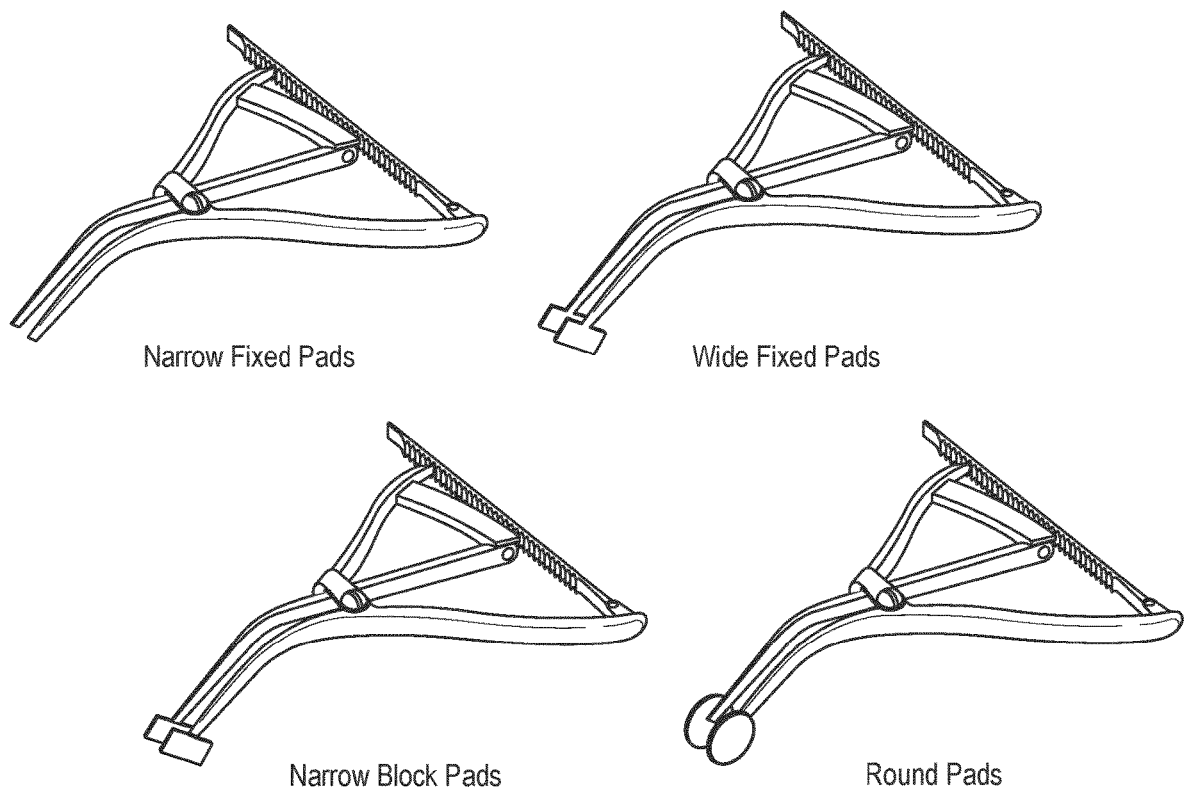
FIG. 3B is a side perspective view of various alternative embodiments of the joint distraction device of FIG. 3A.
Figure 4:
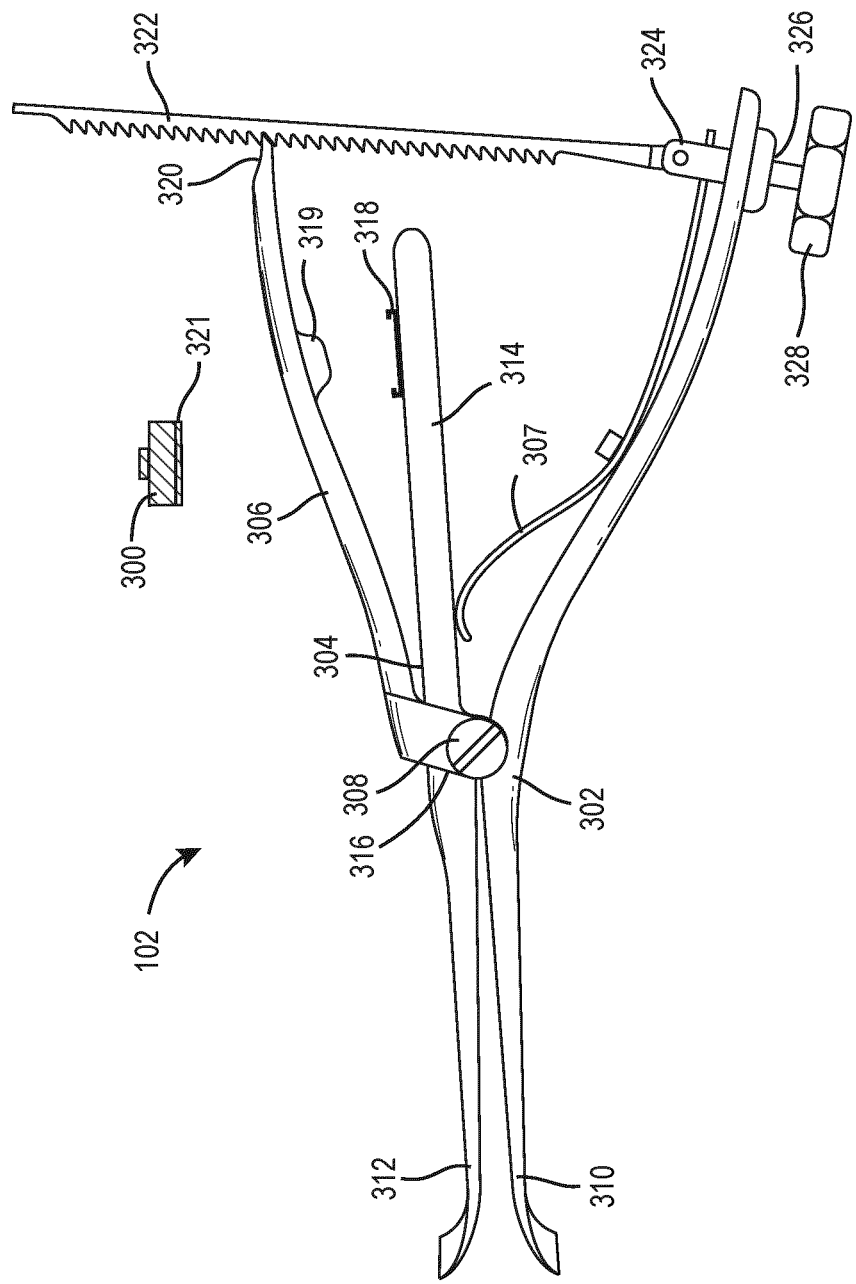
FIG. 4 is a side view of the joint distraction device of FIG. 3 with the disposable force sensor pod decoupled therefrom, according to an exemplary embodiment.

Referring now to FIGS. 3-4, side views of a distraction device 102 and a disposable force sensor pod 300 are shown, according to an exemplary embodiment. FIG. 3 shows the distraction device 102 with the disposable force sensor pod 300 removeably coupled to the distraction device 102 and FIG. 4 shows the disposable force sensor pod 300 decoupled from the distraction device 102. In some embodiments, the distraction device 102 and the disposable force sensor pod 300 are interoperable with the surgical system 200 as described in detail below with reference to FIG. 8.

As shown in FIGS. 3A-4, the distraction device 102 includes a first member (shaft, arm, bar, etc.) 302, a second member 304, and a third member 306 coupled to one another by a hinge 308. The hinge 308 allows rotation of the first member 302, second member 304, and third member 306 relative to one another about the hinge 308. The first member 302, the second member 304, the third member 306, and the hinge 308 may be made of a substantially-rigid, medical-grade, autoclavable (i.e., capable of being sterilized in an autoclave without being damaged) material, for example a metal.

The first member 302 is substantially straight and includes a distal tip 310 configured to engage a first bone (e.g., a tibia). The distal tip 310 may be hooked, curved, etc. away from the substantially straight first member 302. In various embodiments, shown in FIG. 3B, the distal tip includes a narrow fixed pad, a wide fixed pad, a wide block pad, or a round pad. The hinge 308 is shown as positioned at approximately the midpoint of the length of the first member 302. In other embodiments, the hinge 308 is positioned at various other points along the length of the first member 302 (e.g., approximately one-third point, approximately two-thirds point, approximately one-quarter point, approximately three-quarters point, etc.).

The second member 304 includes a distal portion 312 and a proximal portion 314 separated by a corner 316. The second member 304 is coupled to the hinge 308 at the corner 316 (i.e., the corner 316 is coupled to the hinge 308). The second member 304 forms a wide V-shape with the distal portion 312 and the proximal portion 314 angled relative to one another (e.g., separated by an obtuse angle). The distal portion 312 is substantially straight and is configured to engage a second bone (e.g., a femur). The distal portion 312 may include a narrow fixed pad, a wide fixed pad, a wide block pad, or a round pad in various embodiments, as shown in FIG. 3B. The proximal portion 314 is substantially straight. Because the hinge 308 is located between the distal portion 312 and the proximal portion 314, the distal portion 312 rotates away from the first member 302 when the proximal portion 314 is rotated about the hinge 308 towards the first member 302. Accordingly, a downwards (in the orientation shown in FIG. 3A) force on the proximal portion 314 is translated to an upwards force on the distal portion 312.

The proximal portion 314 includes a mount 318 configured to removeably (releaseably, selectively, etc.) couple the disposable force sensor pod 300 to the proximal portion 314.

That is, the mount 318 is configured to receive the force sensor pod 300, hold (secure, etc.) the force sensor pod 300 in position on the proximal portion 314, and release the force sensor pod 300 to allow the force sensor pod 300 to be removed from the distraction device 102 and discarded. For example, the mount 318 may include one or more snaps, latches, hooks, sleeves, tabs, protrusions, channels, etc. The force sensor pod 300 includes a corresponding mounting feature 321 configured to mate with the mount 318 to facilitate the mount 318 in removeably coupling the force sensor pod 300 to the proximal portion 314. For example, the mounting feature 321 of the force sensor pod 300 may include one or more snaps, latches, hooks, sleeves, tabs, protrusions, channels, etc. configured to be interoperable with the one or more snaps, latches, hooks, sleeves, tabs, protrusions, channels, etc. of the mount 318. Accordingly, in various embodiments, the mounting feature 321 and the mount 318 may clip, buckle, snap, slide, etc. together to couple the force sensor pod 300 to the proximal portion 314, and unclip, unbuckle, unsnap, slide in a reverse manner, etc. to decouple the force sensor pod 300 from the proximal portion 314. The mount 318 is configured to allow repeated coupling and decoupling of a force sensor pod 300 to the proximal portion 314.

A biasing member 307 is included in the example shown and extends between the first member 302 and the proximal portion 314. The biasing member 307 has a resilient/springing quality and is configured to lightly force the proximal portion 314 away from the first member 302 (and thereby force the distal portion 312 towards the first member 302).

The third member 306 is manipulable (e.g., by a user) to selectively engage the proximal portion 314 and exert a downwards force on the proximal portion 314 (i.e., a force that pushes the proximal portion 314 towards the first member 302). As shown in FIG. 3A, the third member 306 has a hooked (curved, arcuate, etc.) shape. The third member 306 extends from the hinge 308 to an end 320 of the third member 306, with the proximal portion 314 of the second member 304 positioned between the third member 306 and the first member 302. Rotating the third member 306 towards the first member 302 about the hinge 308 can cause the third member 306 to exert a force on the proximal portion 314 (e.g., cause the third member 306 to contact the proximal portion 314). The force on the proximal portion 314 can cause the proximal portion 314 to rotate towards the first member 302 and the distal portion 312 to rotate away from the first member 302. The position of the third member 306 thereby controls the separation between the distal portion 312 and the distal tip 310 of the first portion 302 (i.e., a distraction distance created by the distraction device 102). Accordingly, a user may operate the distraction device 102 by moving the third member 306 towards the first member 302 to increase the separation between between the distal portion 312 and the distal tip 310 of the first portion 302 and move the third member 306 away from the first member 302 to decrease the separation between the distal portion 312 and the distal tip 310.

As shown in FIG. 3A, the third member 306 includes a protrusion 319 extending from the third member 306 towards the proximal portion 314. The protrusion 319 is configured to contact the force sensor pod 300 coupled to the proximal portion 314. The protrusion 319, the force sensor pod 300, and the mount 318 are configured such that the force exerted on the second member 304 by the third member 306 is transmitted via the protrusion 319 and the force sensor pod 300 when the force sensor pod 300 is coupled to the mount 318. The protrusion 319 pushes on the force sensor pod 300, which transfers the force to the proximal portion 314. Accordingly, the force sensor pod 300 experiences the full force exerted on the proximal portion 314 by the third member 306. The force exerted on the force sensor pod 300 is equal to or proportional to (i.e., depending on the relative dimensions of the proximal portion 314 and distal portion 312) a force exerted by the distal portion 312 and distal tip 310 on a patient's joint.

A ratcheting member 322 is coupled to the first member 302 and is configured to engage the end 320 of the third member 306. The ratcheting member 322 extends substantially orthogonal to the first member 302 and includes a pivot point 324 proximate the first member 302. In this way, the third member 306 can be rotated about the pivot point 324 by a force to increase the angle between the ratcheting member 322 and the first member 302. The ratcheting member 322 engages the biasing member 307 proximate the pivot point 324, and the springing/resilient quality of the biasing member 307 forces the ratcheting member 322 back towards the substantially orthogonal orientation. Accordingly, in the absence of such a force on the ratcheting member 322, the ratcheting member 322 and the first member 302 are returned to substantially orthogonal orientations. The pivot point 324 also allows the ratcheting member 322 to be rotated away from the third member 306 into a disengaged state, where the ratcheting member 322 does not engage the end 320 of the third member 306.

The ratcheting member 322 includes a series of teeth (fins, notches, etc.) located along a first side of the third member 306. Each of the teeth includes a horizontal surface and an angled surface. The horizontal surfaces are substantially parallel to the first member 302, while the angled surfaces connect neighboring teeth in the series. Each horizontal surface is configured to engage the end 320 of the third member 306 and to prevent the end 320 of the third member 306 from rotating further away from the first member 302. Each angled surface allows the end 320 to slide towards the first member 302 along the angled surface to the next horizontal surface (i.e., closer to the first member 302). The springing section 324 of the ratcheting member 322 allows the ratcheting member 322 to open slightly relative to the first member 302 to allow the end 320 to slide along an angled surface. When the end 320 reaches a horizontal surface, the springing section 324 causes the ratcheting member 322 to snap (spring, jump, rotate, etc.) back towards the orthogonal orientation such that the end 320 is held between the horizontal surface and the first member.

The ratcheting member 322 is thereby configured to selectively secure the end 320 of the third member 306 in various positions relative to the first member 302. Because the position of the third member 306 relative to the first member 302 determines the position of the distal portion 312 relative to the distal tip 310 as described above, the ratcheting member 322 thereby facilitates controlled adjustment and maintenance of the amount of separation applied to a joint by the distraction device 102. Furthermore, in the example shown, the ratcheting member 322 is coupled to the first member by a height-adjustment screw 326. The height-adjustment screw 326 is coupled to a handle 328. The handle 328 can be turned to rotate the height-adjustment screw 326 and cause the height adjustment screw to adjust the height of the ratcheting member 322 (i.e., the heights of the horizontal surfaces of the series of teeth) relative to the first member 302. For example, the height-adjustment screw 326 may be configured to allow fine adjustment of the height of the ratcheting member 322 by an amount approximately equal to a size of one of the multiple teeth, i.e., such that the end 320 can be secured by the ratcheting member 322 along a substantially continuous spectrum of positions relative to the first member 302. As another example, the height-adjustment screw 326 allow find adjustment by an amount equal to a size of several (e.g., three, four) of the multiple teeth.

The distraction device 102 is thereby configured for use as follows. The force sensor pod 300 is first mounted on the proximal portion 314. The distal portion 312 of the second member and the distal tip 310 can be inserted into a joint and placed against a pair of bones. For example, the distal tip 310 may be positioned against a tibia and the distal portion 312 may be positioned against a femur. A user (e.g., a surgeon) may then force (e.g., squeeze) the third member 306 towards the first member 302, thereby causing the third member 306 to exert a force on the proximal portion 314 via the force sensor pod 300 which causes the distal portion 312 to move away from the distal tip 310. The force exerted by the user on the third member 306 is thereby transferred to the joint to increase a separation between the two bones (e.g., a femur and a tibia). The user may continue to adjust the separation between the bones, using the ratcheting member 322 and the handle 328 to facilitate fine adjustment of the separation. Meanwhile, the force sensor pod 300 measures the force exerted thereon and provides the force measurements to a computing system as described in detail below. When the third member 306 is held in position relative to the first member 302 (e.g., by the ratcheting member 322), the force exerted on the force sensor pod 300 is proportional to a force exerted on the distal tip 310 and distal portion 312 by the bones, i.e., by the tension in ligaments pulling the bones together. Measurements of ligament tension at various degrees of separation can thereby be collected using the distraction device 102. When the desired measurements are obtained, the distraction device 102 may be removed from the joint. The force sensor pod 300 can be removed from the mount 318 and discarded, and the distraction device 102 (i.e., without a force sensor pod 300) can be sterilized (e.g., using an autoclave) for repeated use with another patient.

Figure 5:
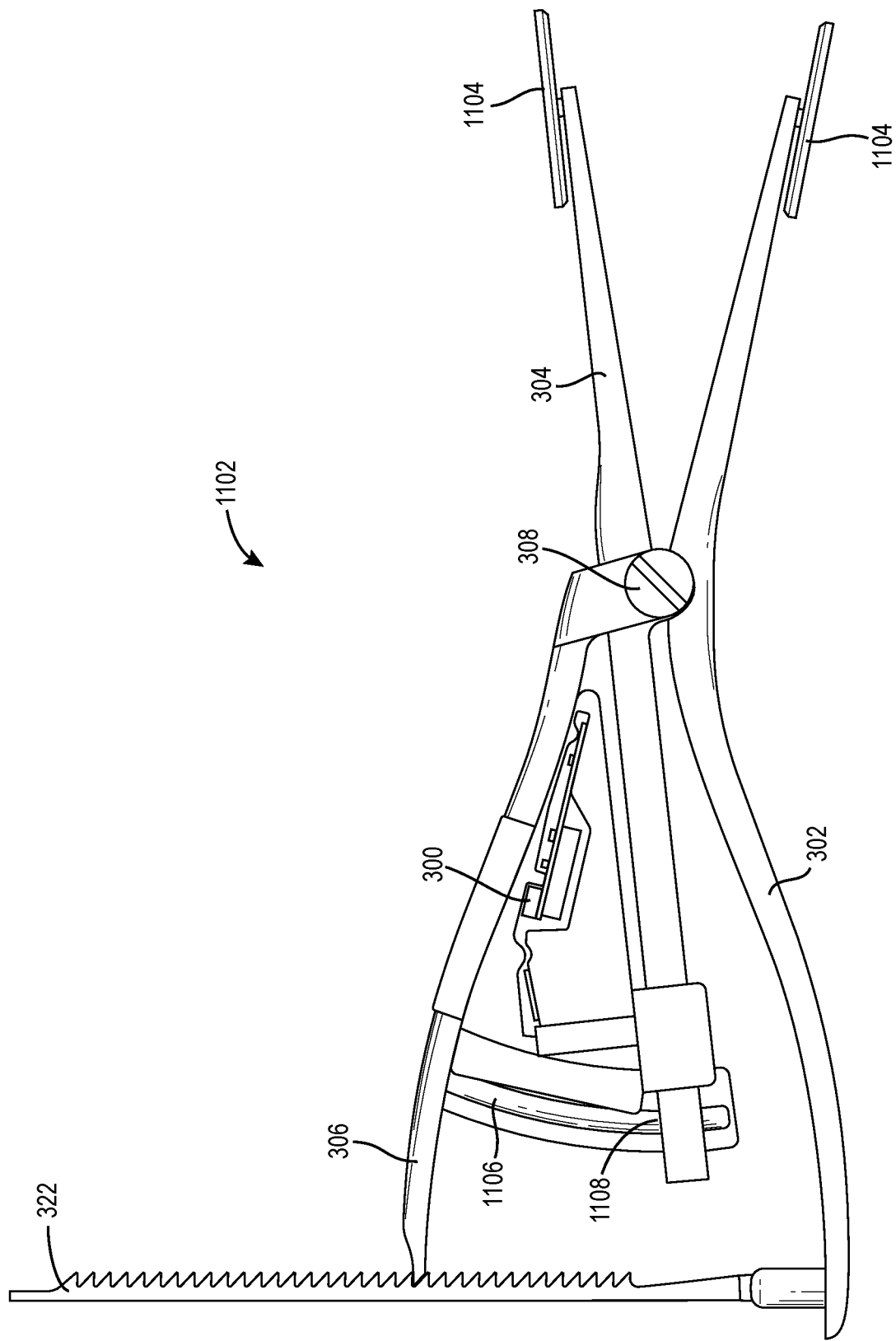
FIG. 5 is a side view of a joint distraction device with a disposable force sensor pod removeably coupled thereto, according to an exemplary embodiment.
Figure 6:
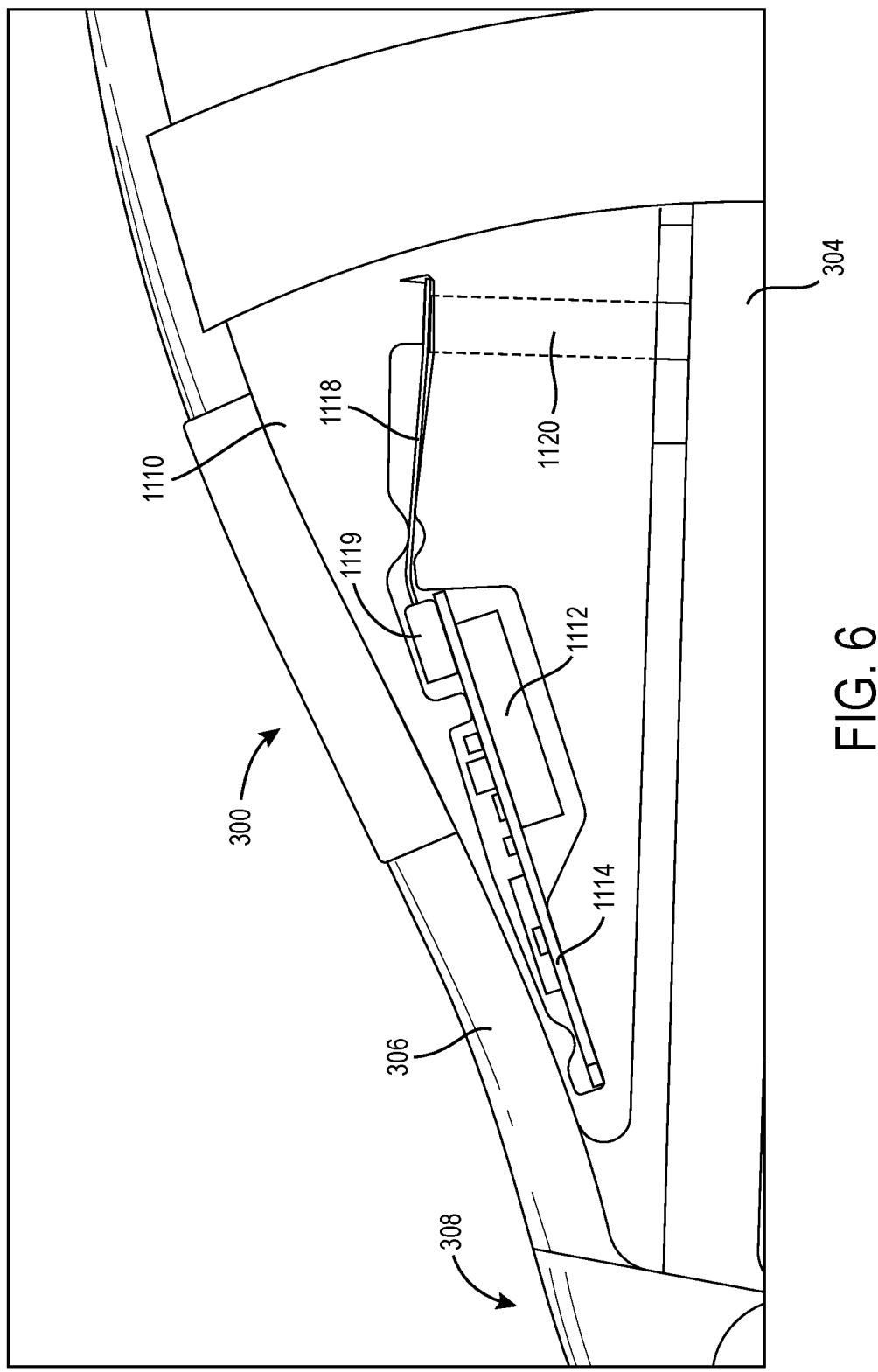
FIG. 6 is a detailed view of the force sensor pod of FIG. 5, according to an exemplary embodiment.

Referring now to FIGS. 5-6, views of another embodiment of a distraction device 1102 with a force sensor pod 300 is shown, according to an exemplary embodiment. The distraction device 1102 of FIGS. 5-6 includes various features found in the distraction device 102, for example the force sensor pod 300, a first member 302, a second member 304, a third member 306, and a ratcheting member 322. In the example of FIGS. 5-6, the second member 304 of the distraction device 1102 is substantially straight through the hinge 308, while the first member 302 is curved or bent with an extremum at the hinge 308. A round pad 1104 is positioned at the distal end of each of the first member 302 and the second member 304. The round pads 1104 are configured to contact bones (e.g., a tibia and a femur).

The distraction device 1102 is shown to include a curved shaft 1106 extending from the third member 306 towards the first member 302. The curved shaft 1106 extends through a channel 1108 (hole, passage, bore, etc.) in the second member 304 and is configured to slide along the channel as the third member 306 rotates relative to the hinge 308. The curved shaft 1106 may have a radius of curvature approximately equal to a distance between the channel 1108 and the hinge 306 such that the curved shaft 1106 can slide through the channel 1108 as the third member 306 is rotated relative to the second member 304 about the hinge 308.

In the example of FIGS. 5-6, the force sensor pod 300 has a substantially triangular housing 1110 that attaches to both the third member 306 and the second member 304. The housing 1110 may include hooks or sleeves configured to allow the housing 1110 to snap onto the third member 306 and/or the second member 304.

FIG. 6 shows the force sensor pod 300 as including a battery 1112, a circuit board 1114, and a force sensor 1116 mounted in the housing 1110. The battery 1112 is coupled to the circuit board 1114 and provides power to the force sensor pod 300 as described below with reference to FIG. 8. The circuit board 1114 may include a communications interface as described below with reference to FIG. 8 and/or various other processing components as desirable in various embodiments. The force sensor 1116 is coupled to the circuit board 1114 and conductively communicable with the circuit board 1114. As shown in FIG. 6, the force sensor 1116 includes a strain member 1118 extending between a base 1119 coupled to the circuit board 1114 and a pole 1120 configured to contact the second member 304. The force sensor 1116 is configured to measure the force or strain on the strain member 1118 exerted thereof by the pole 1120. Such measurements can be correlated to a torque or force exerted between the distal tips of the first member 302 and the second member 304.

Figure 7:
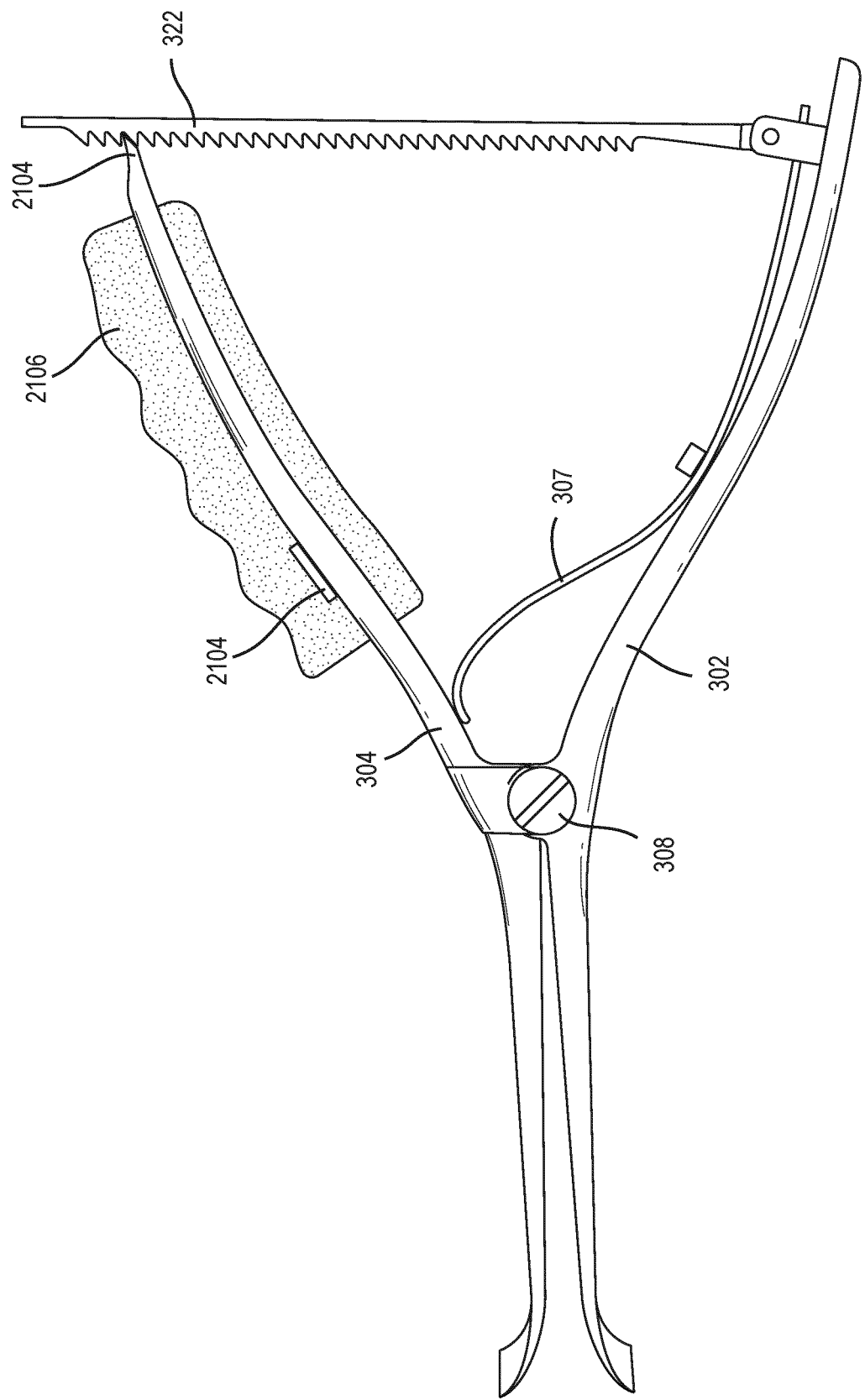
FIG. 7 is a side view of a joint distraction device with a disposable handle, according to an exemplary embodiment.

Referring now to FIG. 7, a distraction device 2102 is shown, according to an exemplary embodiment. The distraction device 2102 includes a first member 302 and a second member 304 rotatably coupled at a hinge 308 in a similar manner as in the distraction device 102 of FIGS. 3-4. In the example of FIG. 7, the first member 302 and the second member 304 are curved such that an extremum of the curvature of each is positioned proximate the hinge 308. The distraction device 2102 also includes a biasing member 307 and ratcheting structure 322 similarly configured as in the distraction device 102 of FIGS. 3-4. As compared to the distraction device 102 of FIGS. 3-4, the third member 306 is omitted, and the ratcheting structure 322 engages a proximal end 2104 of the second member 304.

As shown in FIG. 7, a strain gauge 2104 is coupled to the second member 304, for example integrated with the second member 304 to form a portion of the second member 304. The distraction device 2102 is also shown to include a detachable (disposable) handle casing 2106. The handle casing 2106 may be similar to the force sensor pod 300 and may include a power source, communications interface, and/or other electronic and processing components as desirable in various embodiments. The handle casing 2106 is configured to be selectively attached to the second member 304 such that circuitry housed in the handle casing 2106 is placed in conductive communication with the strain gauge 2104. In such an embodiment, the strain gauge 2104 is reusable (e.g., autoclavable, sterilizable), while the handle casing 2104 and components therein are non-autoclavable and are disposed of and replaced between uses of the distraction device 2102. In other embodiments, the handle casing 2106 includes the strain gauge 2104 such that the strain gauge 2104 is removable and disposable between uses of the distraction device 2102.

In various other embodiments, the strain gauge 2104 or other force sensor is located on or in the ratcheting structure 322, proximate the distal end 312 of the second member 304, or proximate the distal end 314 of the first member 302. It should be understood that many such variations of distractions devices having removable and disposable force sensor pods and/or other disposable electronic components are within the scope of the present disclosure.

Figure 8:
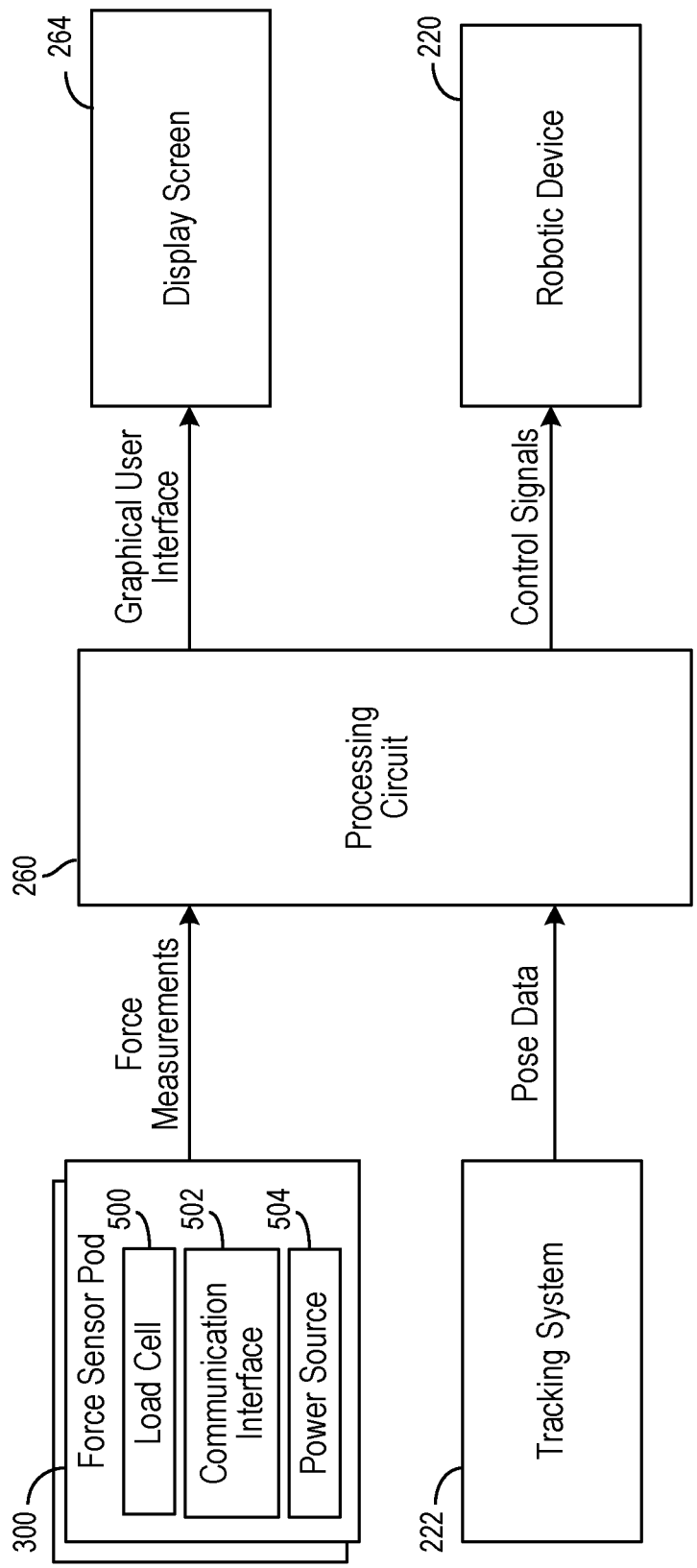
FIG. 8 is a block diagram of the surgical system of FIG. 2 including the disposable force sensor pod of FIG. 3, according to an exemplary embodiment.

Referring now to FIG. 8, a block diagram of the system 200 of FIG. 2 including one or more force sensor pods 300 is shown, according to an exemplary embodiment. As shown in FIG. 8, the system 200 includes the processing circuit 260 in electronic communication with the display screen 264, the robotic device 220, the tracking system 222, and one or more force sensor pods 300. For example, if two distraction devices 102 are used concurrently as in FIG. 1, the processing circuit 260 can be placed in simultaneous electronic communication with both distraction devices. Electronic communications between the force sensor pod 300 and the processing circuit 260 can be wired (e.g., via a cable physically coupled to the force sensor pod 300 and the processing circuit 260) or wireless (e.g., via WiFi, Bluetooth, etc.).

The force sensor pod 300 is shown to include a load cell 500, a communication interface 502, and a power source 504. The load cell 500, the communication interface 502, and the power source 504 are communicably coupled to one another and may be positioned within and/or at a boundary of a housing of the force sensor pod 300. In the embodiment shown, the load cell 500, the communication interface 502, and the power source 504 are all removable from and replaceable on the distraction device 102. In other embodiments, the load cell 500 is reusable and integrated with the distraction device 102, while the communication interface 502 and the power source 504 are removable from and replaceable on the distraction device 102. In other embodiments, the load cell 500 and the communication interface 502 are reusable and fixedly coupled to the distraction device 102, while the power source 504 is removable from the force sensor pod 300 and/or the distraction device 102 and can be replaced for later uses (e.g., to extend lifetime of a battery-powered force sensor pod 300). Various such combinations of removable/replaceable components and reusable/autoclavable components are possible, and all such combinations are within the scope of the present disclosure.

The force sensor pod 300 is configured such that the load cell 500 experiences substantially the entire force (or a constant proportion thereof) exerted on the second member 304 by the third member 306 via the force sensor pod 300 when the force sensor pod 300 is coupled to the second member 304. The load cell 500 measures the force exerted on the force sensor pod 300. That is, the load cell 500 is configured to generate an electrical signal (e.g., analog signal) indicative of the force exerted on the load cell 500. The load cell 500 may be a piezoelectric load cell, a capacitive load cell, or a strain gauge load cell.

The load cell 500 provides the measurement (i.e., the electrical signal indicative of the force exerted on the load cell 500) to the communication interface 502. The communication interface 502 may include an amplifier configured to amplify an analog signal from the load cell 500. In some embodiments, the communication interface 502 includes a port or conductive contact configured to transfer the measurement to a cable coupled to the communication interface 502 and the processing circuit 260. In other embodiments, the communication interface 502 includes a wireless communications interface, for example a Bluetooth or WiFi transceiver. In some such embodiments, the communication interface 502 is configured to convert an analog signal from the load cell to a digital signal suitable for transmission via a wireless network. Advantageously, wireless communications reduce clutter in the surgical field and remove the need for a cable extending across the boundary between the sterile field and the non-sterile field during an operation.

The power source 504 is configured to provide electrical power to the load cell 500 and/or communication interface 502 as needed for operation of the load cell 500 and/or communication interface 502. In some embodiments, the power source 504 includes a battery. In some embodiments, the power source 504 includes a port or conductive contact configured to receive power via a cable connected to an external power source. For example, in some embodiments, a single cable includes a first cord configured to provide electrical power to the force sensor pod 300 and a second cord configured to transmit force measurements from the force sensor pod 300 to the processing circuit 260.

As described above, the tracking system 222 can collect and provide data relating to the pose (position and orientation) of anatomical structures, for example bones distracted by the distraction device 102. For example, in the examples shown herein relating to TKA or PKA procedures, the tracking system 222 collects and provides data indicative of the relative poses of a femur 206 and a tibia 208 to the processing circuit 260. The pose data generated by the tracking system 222 is indicative of the relative orientations of the femur 206 and the tibia 208, i.e., of a current angle within a range of motion of the joint. When one or more distraction devices 102 are used to distract the knee joint, the pose data generated by the tracking system 222 is indicative of the amount of separation created by the distraction device(s) 102 (i.e., a distance between the femur 206 and the tibia 208 at the joint).

The processing circuit 260 is configured to receive the force measurements from the force sensor pod 300 (i.e., from the load cell 500 via the communication interface 502) and the pose data from the tracking system 222 as illustrated in FIG. 8.

The processing circuit 260 is configured to associate one or more force measurements (i.e., from one or more force sensor pods 300) for a time step (i.e., for a particular point in time) with pose data for that time step. The processing circuit 260 thereby acquires a ligament tension associated with a pose of the femur relative to a pose of the tibia (i.e., a relative angle/orientation and a distance of separation). The processing circuit 260 is configured to collect (store) force measurements and pose data over time to generate a dataset. In some embodiments, in order to acquire a dataset that includes a sufficient (desired, necessary, preferable, useful, etc.) amount of relevant data, the processing circuit 260 may be configured to generate instructions directing a surgeon to operate the distraction device(s) 102 through a range separation distances and manipulate the femur and tibia through a range of poses. In such embodiments, the processing circuit 260 can cause the display screen 264 to display such instructions.

In some embodiments, the processing circuit 260 generates a graphical user interface that includes force measurements and/or pose data and controls the display screen 264 to display the graphical user interface. In some embodiments, the force measurements and/or pose data are displayed as real-time raw data (i.e., a current force measurement). In other embodiments, a graph (chart, plot, etc.) of force measurements and/or pose data is shown. For example, a graph of force (i.e., ligament tension) versus joint separation may be shown. Various graphical representations are possible. A surgeon may use the data displayed on the graphical user interface to make various decisions regarding implant size, implant placement, surgical planning, ligament release, etc.

Figure 9:
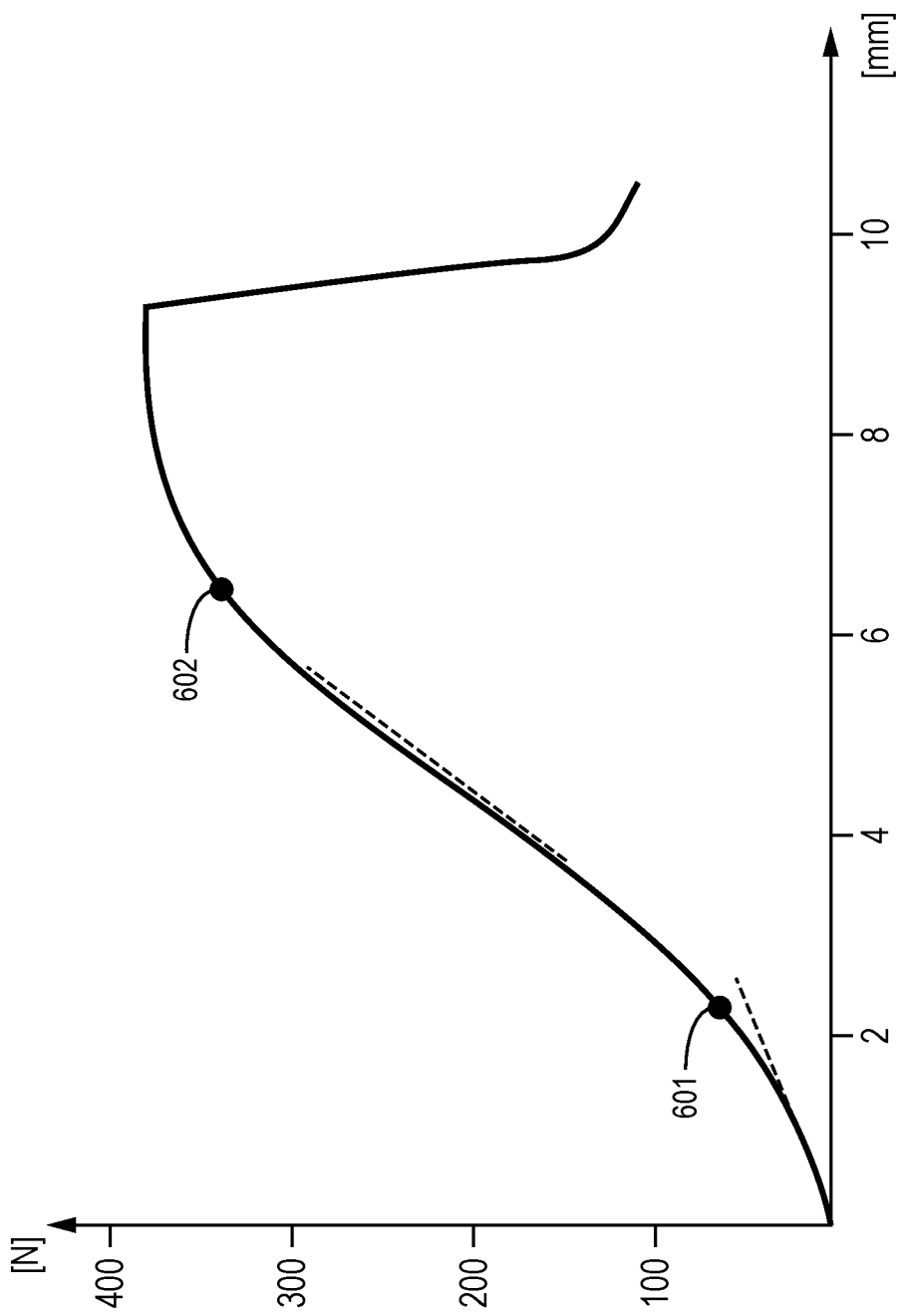
FIG. 9 is a graph of ligament tension, according to an exemplary embodiment.

In some embodiments, the processing circuit 260 is configured to automatically detect one or more characteristics of the ligament tension. As one example, transition points of the ligament stiffness may be determined by the processing circuit 260. FIG. 9, described below, shows an example graph of ligament tension as a function of joint displacement/separation. While the following discussion of the stiffness transition points refers specifically to the knee joint and to the tibia and femur, it should be understood that the same or similar concepts are applicable to evaluation of soft tissue of any joint. The processing circuit 260 may be configured to determine the first transition point of the ligament stiffness in a variety of relative orientations of the femur and tibia using data from the force sensor pod(s) 300 and the tracking system 222.

FIG. 9 shows a typical force displacement curve of a ligament of a knee joint. The curve depicts four characteristic behaviors of the ligaments as they are stretched. The first zone depicts the transition from slackness to high stiffness which occurs the first transition point 601, where all fibers of the ligament are engaged in stress sharing. A second zone, between the first transition point 601 and the second transition point 602, shows a substantially linear behavior of ligament stiffness over a wide range of force until transitioning (at the second transition point 602) into a third zone where fibers begin to fail, therefore diminishing its stiffness. This is followed by its rupture and complete failure depicted in the fourth zone at the end of the curve.

The region between the two stiffness transition points 601, 602 is a region of high, substantially linear ligament stiffness. Typical soft tissue assessments methods employ an arbitrary load in this segment to assess soft tissue stability. However, the stiffness transition points are patient-specific, such that utilizing a preset, arbitrary load may result in improper soft tissue balancing. Improper soft-tissue balancing may result in a too-loose configuration which will lead to knee instability for the patient, or a too-tight configuration which could lead to pain for the patient after the surgical procedure.

Accordingly, in some embodiments, the processing circuit 260 is configured to identify the first stiffness transition point 601 of the soft tissue of the knee across its entire range of motion or for multiple discrete relative poses within the range of motion using data collected by the force sensor pod(s) 300 and the tracking system 222. The processing circuit 260 may cause the display screen 264 to display instructions that instruct a surgeon to manipulate the femur, tibia, and distraction device(s) 102 as needed to collect the data necessary to determine the first stiffness transition point 601 across the range of motion. The processing circuit 260 can collect and associate force measurements and relative poses of the femur and tibia, as described above, through a range of motion of the knee and through a safe range of distraction/separation distances, and automatically process the data to determine the first stiffness transitions points. For example, the processing circuit 260 may use the second derivative of the curve shown in FIG. 9 to automatically detect a separation distance at which the linearly-increasing second zone begins. For example, the display screen 264 may display instructions for the user to start at a low force applied by the distraction device(s) 102 and then increase the force to pass through the stiffness transition point. The display screen 264 may also display instructions to decreases the force from above the stiffness transition point to below the stiffness transition point. The processing circuit 260 may cause the display screen 264 to instruct the user to perform various such trials by ramping the force up and down past the stiffness transition point until a satisfactory amount of data is ascertained to provide a confident calculation of the stiffness transition point.

The processing circuit 260 may then use the first stiffness transitions points to facilitate appropriate ligament balancing in the surgical procedure. For example, as described above, the processing circuit 260 is configured to establish a surgical plan for modifying the tibia and femur and for placement of prosthetic implant components. In some embodiments, the processing circuit 260 is configured to modify (adjust, fine-tune, update, etc.) the surgical plan in accordance with the determined stiffness transition points, i.e., by selecting the size/position of implants and/or the depth of cuts based on the stiffness transition points. In some embodiments, the processing circuit 260 performs such modifications automatically. In other embodiments, stiffness transition point information is provided to a surgeon via a planning interface to facilitate the surgeon in manually adjusting the surgical plan via the planning interface. Measurements can be collected and analyzed at multiple stages of a surgical procedure to facilitate multiple intra-operative updates to a surgical plan.

The processing circuit 260 thereby facilitates use of the measurements from the force sensor pod(s) 300 and the tracking system 222 to optimize the positions of prosthetic components, bone modifications, and/or soft tissue modifications to increase the likelihood of proper ligament balancing.

As mentioned above with reference to FIG. 2, the processing circuit 260 is configured to control the robotic device 220 in accordance with the surgical plan. The control approaches (e.g., virtual objects, haptic boundaries, autonomous control, surgical navigation, etc.) described above are also applicable to surgical plans established and/or updated as described with reference to FIGS. 8-9. That is, measurements collected using one or more distraction devices 102 coupled to one or more force sensor pod(s) 300 may be used to adjust the surgical plan executed by the robotic device 220. Accordingly, the robotic device 220 can be controlled in accordance with measurements from the one or more force sensor pod(s) 300.

Figure 10:
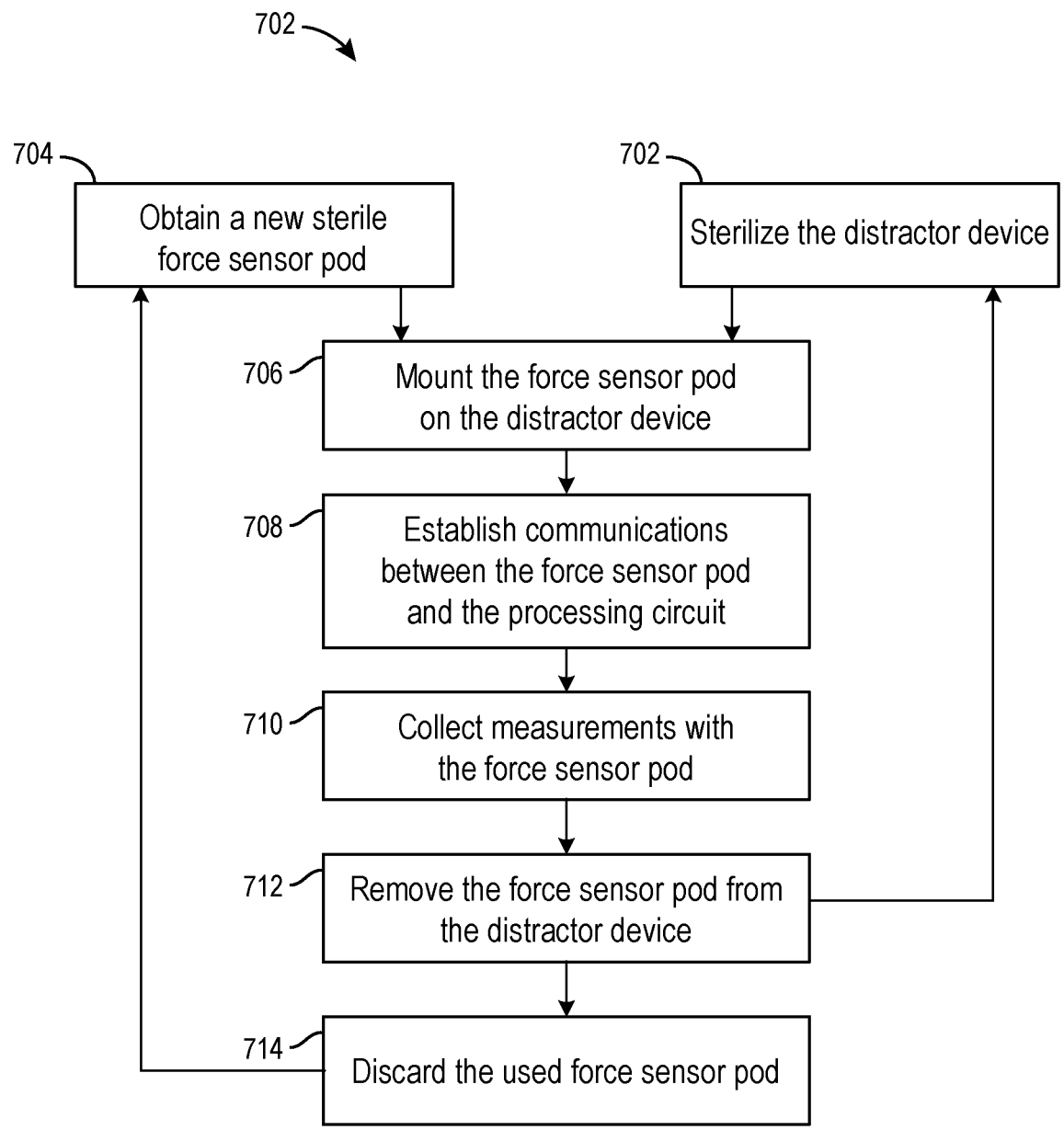
FIG. 10 is a flowchart of a process of using the joint distraction device and disposable force sensor pod of FIGS. 3-4, according to an exemplary embodiment.

Referring now to FIG. 10, a flowchart of a process for using a distraction device 102 is shown, according to an exemplary embodiment. In the examples shown herein, the force sensor pod 300 is disposable. That is, the force sensor pod 300 is not suitable to be re-sterilized after use, such that the force sensor pod 300 can be used with a single patient before being discarded. Because the force sensor pod 300 is disposable (e.g., non-autoclavable), the force sensor pod 300 can be cheaper and easier to manufacture than a load cell engineered to withstand repeated re-sterilization. Additionally, because the force sensor pod 300 is removable from the distraction device 102, only the force sensor pod 300 needs to be replaced after use while the distraction device 102 can be re-sterilized for repeated use. This avoids the waste and associated with force-sensing devices which need to be fully replaced after every use. The force sensor pod 300 and the distraction device 102 may thereby achieve a preferable cost, safety, and efficiency balance by combining both a single-use (disposable) component and a reusable (sterilizeable) component.

At step 702, the distractor device 102 is sterilized, for example in an autoclave using conventional sterilization techniques. At step 704, a new sterile force sensor pod 300 is obtained. For example, the force sensor pod 300 may be packaged manufactured in a sterile environment and sealed in protective packaging until opened at step 704.

At step 706, the force sensor pod 300 is mounted on the distractor device 102. In the example of FIGS. 3-4, the mounting feature 321 engages the mount 318 of the second member 304 to couple the force sensor pod 300 to the distractor device 102. The force sensor pod 300 may also be activated at step 706 (e.g., the power source 504 may begin providing power to the communication interface 502 and/or the load cell 500).

At step 708, communications are established between the force sensor pod 300 and the processing circuit 260. For example, in an embodiment using wired communications, a cable may be connected between the force sensor pod 300 and the processing circuit 260. The cable is sterile such that the cable can safely extend into the surgical field while connected to the force sensor pod 300. As another example, in an embodiment using wireless communications, the processing circuit 260 detects the presence of the force sensor pod 300 and establishes a wireless communication channel therebetween.

At step 710, measurements are collected with the force sensor pod 300. That is, a surgeon manipulates the distraction device 102 to distract a joint while the force sensor pod 300 measures the forces exerted on the force sensor pod 300 and provides the measurements to the processing circuit 260. The processing circuit 260 may also receive pose data from the tracking system 222 as described above.

When measurements are complete, at step 712 the force sensor pod 300 is removed (decoupled) from the distractor device 102. That is, in the example of FIGS. 3-4, the mount 318 releases the mounting feature 321 of the force sensor pod 300 so that the force sensor pod 300 can be separated from the second member 304. At step 714, the force sensor pod 300 used in steps 706-712 is discarded, for example in a bio-hazard safe receptacle.

Unlike the force sensor pod 300, the distraction device 102 is not discarded. Instead, the distraction device 102 can be re-sterilized for future use at step 702. The process 700 can be restarted (e.g., for a different patient) by re-sterilizing the distraction device 102 at step 702 and acquiring a new (different) force sensor pod 300 at step 704. Accordingly, over multiple iterations of process 700, multiple force sensor pods 300 are used with a single distraction device 102. In some cases, a kit may be assembled that includes multiple force sensor pods with one distraction device 102 to facilitate repeated execution of process 700.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

What is claimed is:

1. A joint distraction device, comprising:
   a first member;
   a hinge coupled to the first member;
   a second member comprising a distal portion and a proximal portion, the second member coupled to the hinge at a position between the distal portion and the proximal portion;
   a third member coupled to the hinge and manipulable to exert a force on the proximal portion of the second member that causes the distal portion to rotate away from the first member; and
   a disposable force sensor pod configured to be removeably coupled to at least one of the second member or the third member;
   wherein the second member comprises a mount configured to removably couple the disposable force sensor pod to the proximal portion; and
   the third member comprises a protrusion configured to exert the force on the second member via the force sensor pod when the disposable force sensor pod is coupled to the mount.

2. The joint distraction device of claim 1, wherein the first member is configured to engage a first bone and the distal portion of the second member is configured to engage a second bone;
   and wherein the force exerted on the proximal portion of the second member by the third member is proportional to a distraction force provided by the first member and the distal portion to distract the first bone from the second bone.

3. The joint distraction device of claim 1, wherein the third member extends from a first end of the third member positioned proximate the hinge to a second end of the third member, the distraction device comprising:
   a ratcheting structure coupled to the first member and configured to engage the second end of the third member.

4. The joint distraction device of claim 3, wherein the ratcheting structure is coupled to a threaded head configured to facilitate fine adjustment of a position of the ratcheting structure.

5. A joint distraction device, comprising:
   a first member;
   a hinge coupled to the first member;
   a second member comprising a distal portion and a proximal portion, the second member coupled to the hinge at a position between the distal portion and the proximal portion;
   a third member coupled to the hinge and manipulable to exert a force on the proximal portion of the second member that causes the distal portion to rotate away from the first member; and
   a disposable force sensor pod configured to be removeably coupled to at least one of the second member or the third member;

wherein the second member comprises a mount configured to removably couple the disposable force sensor pod to the proximal portion; and wherein the disposable force sensor pod comprises a pole configured to contact the second member, the disposable force sensor pod configured to measure the force exerted on the pole.

6. A surgical system, comprising:

a joint distraction device comprising:

a first member;

a hinge coupled to the first member;

a second member comprising a distal portion and a proximal portion, the second member coupled to the hinge at a position between the distal portion and the proximal portion;

a third member coupled to the hinge and manipulable to exert a force on the proximal portion of the second member that causes the distal portion to rotate away from the first member;

a disposable force sensor pod comprising a mounting feature and at least one of a load cell or a strain gauge;

a computing system configured to be placed in electronic communication with the disposable force sensor pod and receive a force measurement from the disposable force sensor pod;

wherein the disposable force sensor pod is configured to be removably coupled to at least one of the second member or the third member of the distraction device by the mounting feature; and wherein the proximal portion of the second member comprises a mount configured to receive the mounting feature of the disposable force sensor pod, the mount positioned on a surface of the proximal portion facing the third member.

7. The system of claim 6, wherein the distraction device is autoclavable.

8. The system of claim 6, wherein the disposable force sensor pod is non-autoclavable.

9. The system of claim 6, comprising a plurality of replacement disposable force sensor pods.

10. The system of claim 6, wherein the distraction device is operable to distract a first bone from a second bone, the system further comprising a tracking system configured to track a pose of the first bone and a pose of the second bone.

11. The system of claim 10, wherein the computing system is configured to associate, for each of a plurality of time steps, the force measurement from the disposable force sensor pod for the time step with a distraction distance calculated based on the pose of the first bone for the time step and the pose of the second bone for the time step.

12. The system of claim 11, comprising a display screen, the display screen configured to display a graphical representation of the distraction distance and the force measurement for the plurality of time steps.

13. The system of claim 12, wherein the computing system is configured to identify at least one of a preferred distraction distance or a ligament stiffness transition point by analyzing the force measurements and the distraction distances for the plurality of time steps.

14. The system of claim 13, wherein the computing system is configured to generate or modify a surgical plan in accordance with the preferred distraction distance.

15. The system of claim 14, comprising a robotic device; wherein the computing system is configured to control the robotic device in accordance with the surgical plan.

16. The system of claim 6, wherein the electronic communication comprises wireless communication.

17. A surgical system, comprising:

a joint distraction device comprising:

a first member;

a hinge coupled to the first member;

a second member comprising a distal portion and a proximal portion, the second member coupled to the hinge at a position between the distal portion and the proximal portion;

a third member coupled to the hinge and manipulable to exert a force on the proximal portion of the second member that causes the distal portion to rotate away from the first member;

a disposable force sensor pod comprising a mounting feature and at least one of a load cell or a strain gauge, wherein the disposable force sensor pod is configured to be removably coupled to at least one of the second member or the third member of the distraction device by the mounting feature;

a computing system configured to be placed in electronic communication with the disposable force sensor pod and receive a force measurement from the disposable force sensor pod; and a disposable cord coupled to the disposable force sensor pod and the computing system, the disposable cord configured to provide a conductive path for the electronic communication.

18. The system of claim 17, comprising a plurality of replacement disposable force sensor pods.

19. A method, comprising:

sterilizing a distraction device, wherein the distraction device comprises a first member, a hinge coupled to the first member, a second member comprising a distal portion and a proximal portion wherein the second member is coupled to the hinge at a position between the distal portion and the proximal portion, and a third member coupled to the hinge and manipulable to exert a force on the proximal portion of the second member that causes the distal portion to rotate away from the first member;

obtaining a sterile package containing a disposable force sensor pod;

removing the disposable force sensor pod from the sterile package;

coupling the disposable force sensor pod to at least one of the second member or the third member of the distraction device;

establishing electronic communication between the disposable force sensor pod and a computing system using a disposable cord coupled to the disposable force sensor pod, the disposable cord providing a conductive path for the electronic communication; and wherein the proximal portion of the second member comprises a mount configured to receive the mounting feature of the disposable force sensor pod, the mount positioned on a surface of the proximal portion facing the third member.

20. The method of claim 19, comprising:

performing a knee distraction using the distraction device;

receiving, by the computing system, measurements of a distraction force applied by the distraction device from the disposable force sensor pod;

decoupling the disposable force sensor pod from the distraction device;
discarding the disposable force sensor pod;
re-sterilizing the distraction device; and
obtaining a second sterile package containing a second disposable force sensor pod.

\* \* \* \* \*